US00PP16859P3

(12) United States Plant Patent
Jamieson

(10) Patent No.: US PP16,859 P3
(45) Date of Patent: Jul. 25, 2006

(54) STRAWBERRY VARIETY NAMED 'BRUNSWICK'

(50) Latin Name: *Fragaria ananassa*
Varietal Denomination: Brunswick

(75) Inventor: Andrew R. Jamieson, Nova Scotia (CA)

(73) Assignee: Her Majesty the Queen in Right of Canada, as represented by the Minister of Agriculture and Agrifood, Atlantic Food and Horticulutre Research Centre, Agriculture and Agri-Food Canada, Nova Scotia (CA)

( * ) Notice: Subject to any disclaimer, the term of this patent is extended or adjusted under 35 U.S.C. 154(b) by 65 days.

(21) Appl. No.: 10/770,360

(22) Filed: Feb. 2, 2004

(65) Prior Publication Data

US 2004/0231019 P1 Nov. 18, 2004

Related U.S. Application Data

(63) Continuation of application No. 10/073,438, filed on Feb. 11, 2002, now abandoned.

(51) Int. Cl.
*A01H 5/00* (2006.01)

(52) U.S. Cl. ..... Plt./208

(58) Field of Classification Search ..... Plt./208
See application file for complete search history.

(56) References Cited

PUBLICATIONS

UPOV–ROM GTITM Computer Database 2004/04, GTI Jouve Retrieval Software, Citation for 'Brunswick'.*

* cited by examiner

*Primary Examiner*—Anne Marie Grunberg
*Assistant Examiner*—Annette H Para
(74) *Attorney, Agent, or Firm*—The Webb Law Firm

(57) ABSTRACT

This invention relates to a new and distinct variety of strawberry (*Fragaria ananassa*) named 'Brunswick' characterized by its large petals, large calyx, ovoid fruit, and resistance to powdery mildew. The invention is distinct from other varieties, but most similar to 'Cavendish' and 'Honeoye'.

2 Drawing Sheets

Botanical classification: *Fragaria ananassa.*
Varietal denomination: 'Brunswick'.

BACKGROUND OF THE INVENTION

The present invention includes a new and distinct cultivar of *Fragaria ananassa* known by the varietal name 'Brunswick', originally designated as "K90-12". The new variety resulted from a controlled cross in an ongoing breeding program between the strawberry plants 'Cavendish' (U.S. Plant Pat. No. 11,110) and 'Honeoye' (unpatented). 'Cavendish' was developed by the Atlantic Food and Horticulture Research Centre (a facility of Agriculture and Agri-Food Canada) in Kentville and 'Honeoye' was developed by the New York State Agricultural Experiment Station in Geneva. 'Brunswick' was discovered in 1990 as a seedling in a controlled breeding plot near Sheffield Mills, Nova Scotia at the Sheffield Farm, a field-station of the Atlantic Food and Horticulture Research Centre, where it was selected and propagated asexually by stolons at the Atlantic Food and Horticulture Research Centre in Kentville. Asexual propagules from this original source have been produced annually in a greenhouse at the Atlantic Food and Horticulture Research Centre, Kentville, Canada. 'Brunswick' has been tested at the Atlantic Food and Horticulture Research Centre (starting in 1991) and also at research centres in Charlottetown, Prince Edward Island, Buctouche, New Brunswick, Fredericton, New Brunswick, and Pynn's Brook, Newfoundland, all of Canada. This propagation and testing has demonstrated that the combination of traits disclosed herein which characterize the new variety are fixed and retained true to type through successive generations of asexual reproduction via stolons.

DESCRIPTION OF THE PLANT

Figure 1:
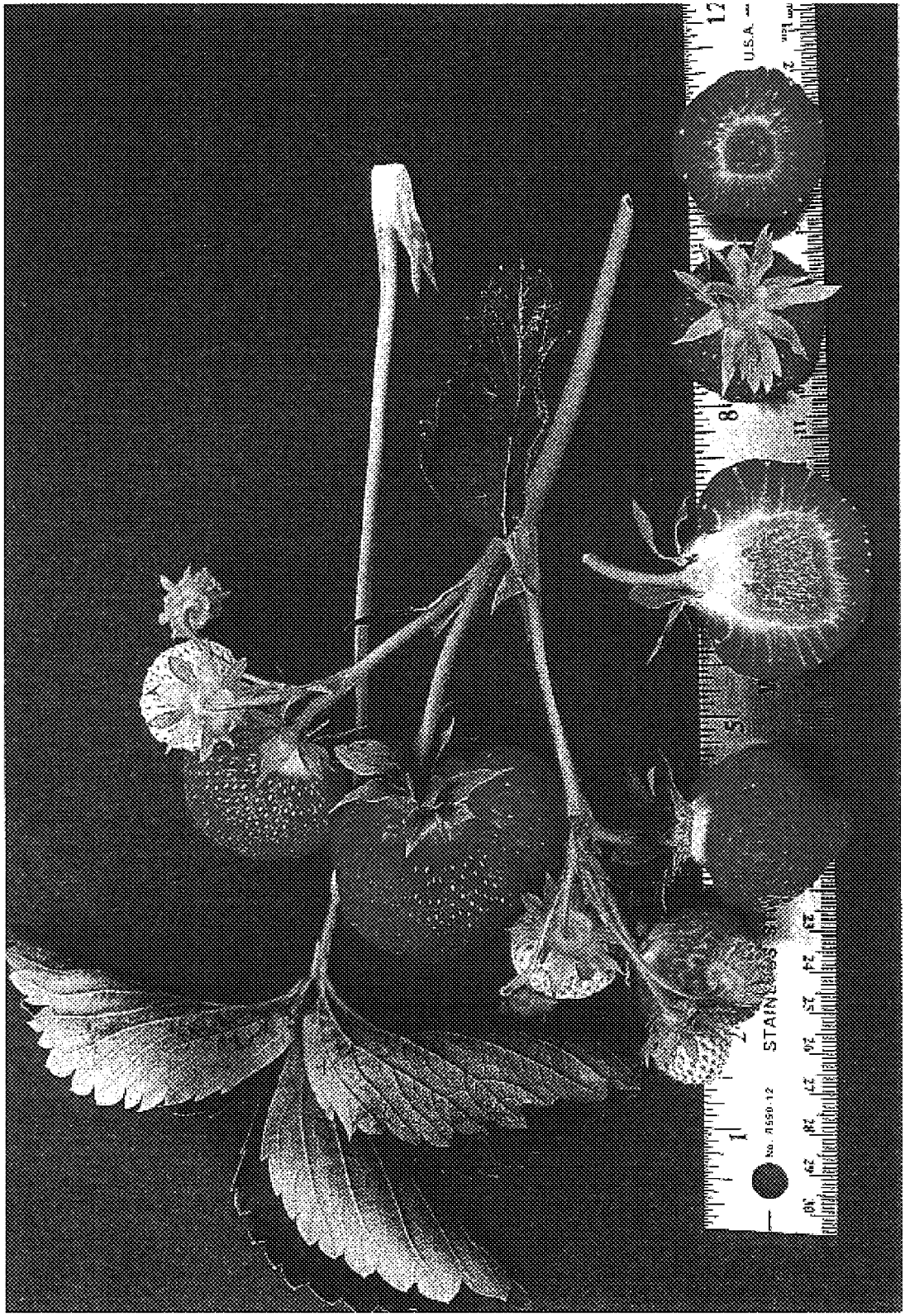
FIG. 1 shows plant parts of the new variety, typical in size, shape, and color.
Figure 2:
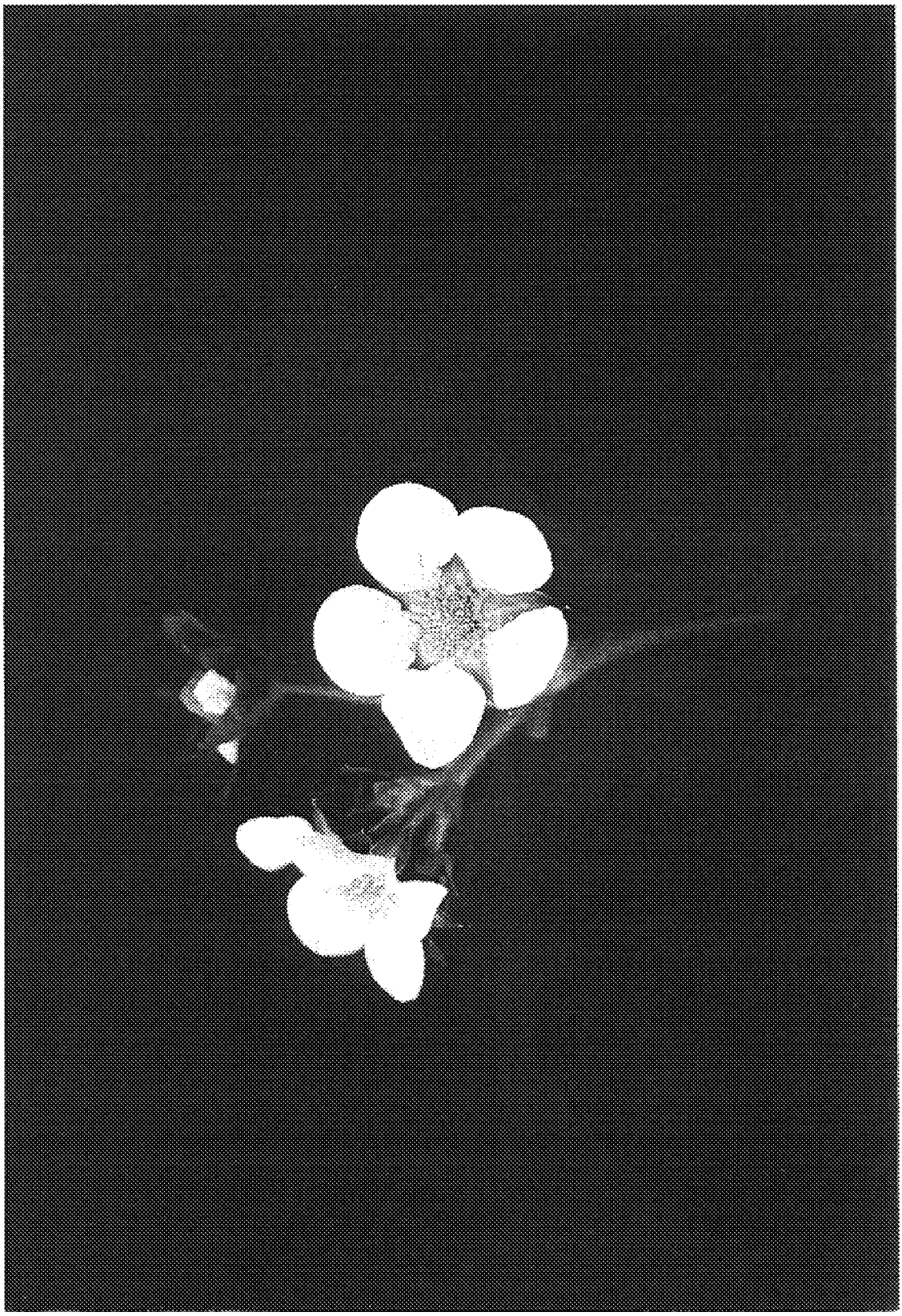
FIG. 2 shows the flowers of the new variety.

The following detailed botanical description of the new variety is based upon measurements and observations taken of plants and fruit grown in Kentville, Nova Scotia, Canada. Observations were taken from each variety as grown in a side-by-side field trial. Color designations, color descriptions, and other phenotypical descriptions may deviate from the stated values and description depending upon variation in the environment, seasonal, climatic and cultural conditions, however, it is believed that this description will apply to the 'Brunswick' plants grown in similar conditions of soil and climate elsewhere. Color references generally are made to R.H.S. Colour Chart of The Royal Horticultural Society of London (1966 edition). Descriptive information on the new variety is presented in Tables 1 and 2. In the tables, the flowers described are secondary flowers. The fruit described is the secondary fruit of the maiden crop, thirteen or fourteen months after planting. The harvest data in Table 3 is based on a complete harvest of the crop. Principal differences between 'Brunswick', the patented variety 'Cavendish' and the unpatented variety 'Honeoye' are set forth herein. Further, several differences between 'Brunswick' and 'Cavendish' and 'Honeoye' include:

1. 'Brunswick' has more dense petiole pubescence;
2. 'Brunswick' has a later beginning of the flowering period;
3. 'Brunswick' produces more flowers per truss and has a longer flower truss;
4. 'Brunswick' has broader fruit;
5. 'Brunswick's' petals are longer than they are wide, whereas the petals of the reference varieties are as long as they are wide; and
6. 'Brunswick's' inner calyx is smaller than the outer calyx, whereas the inner and outer calyces of the reference varieties have the same diameter.

Classification: The new variety is botanically identified as *Fragaria ananassa* and commercially classified as a short-day strawberry.

Plant and foliage characteristics: When propagated in the nursery, 'Brunswick' produces moderate numbers of runner plants, similar to 'Cavendish' but less than 'Honeoye'. Individual plants of all three varieties are medium in size. The plants of 'Brunswick' are of medium density with globose habit and strong vigor. 'Brunswick' rows are less dense and more open than rows of 'Honeoye', but more dense than 'Cavendish'. As shown in Table 1, leaf color of 'Brunswick', 'Cavendish' and 'Honeoye' are Green Group 137A on the upper surface. The color of the lower surface of 'Brunswick' and 'Honeoye' is Green Group 138B but Green Group 137C for 'Cavendish'. Leaflets of 'Brunswick' are larger than 'Cavendish' and slightly larger than 'Honeoye' and leaves of all three varieties have three leaflets. Leaflets of 'Brunswick' and 'Cavendish' are cupped whereas 'Honeoye' leaflets are flat. Leaflets of 'Brunswick' and 'Cavendish' have higher numbers of serrations than 'Honeoye'. Leaflet serrations of 'Brunswick' and 'Honeoye' are semi-round whereas serrations of 'Cavendish' are rounded. The venation of 'Brunswick' leaflets is pinnate. Petiole pubescence for 'Brunswick' tends to be higher in density than for 'Cavendish' and 'Honeoye' but all three varieties have a perpendicular orientation of the pubescence.

TABLE 1

Foliar Characteristics for 'Brunswick', 'Cavendish' and 'Honeoye'

| | Cultivar | | |
|---|---|---|---|
| Foliar Character | 'Brunswick' | 'Cavendish' | 'Honeoye' |
| Leaf color | Green Group | Green Group | Green Group |
| Upper surface | 137A | 137A | 137A |
| Lower surface | 138B | 137C | 138B |
| Central leaflet | | | |
| Length (mm) | | | |
| Mean | 87.8 | 79.9 | 83.8 |
| Range | 80–100 | 64–89 | 65–97 |
| Width (mm) | | | |
| Mean | 77.0 | 74.6 | 70.3 |
| Range | 65–95 | 55–90 | 55–87 |
| Length/width ratio | 1.14 | 1.07 | 1.19 |
| No. leaflets/leaf | 3 | 3 | 3 |
| Leaf convexity | cupped | cupped | flat |

TABLE 1-continued

Foliar Characteristics for 'Brunswick', 'Cavendish' and 'Honeoye'

| | Cultivar | | |
|---|---|---|---|
| Foliar Character | 'Brunswick' | 'Cavendish' | 'Honeoye' |
| Serrations | | | |
| Number | many | many | moderate |
| Size | medium | medium | small |
| Shape | semi-round | rounded | semi-round |
| Tip serration size | small | small | small |
| Leaf pubescence | medium | medium | medium |
| Petiole pubescence | | | |
| Density | medium to dense | medium | medium |
| Direction | perpendicular | perpendicular | perpendicular |

Flower and fruit characteristics: The length of bloom for 'Brunswick' is about three weeks when grown in Kentville, Nova Scotia, Canada in a matted row cultural system. 'Brunswick' typically has 2 to 4 crowns when counted at bloom time of the first harvest season. Flowering for 'Brunswick' typically begins on June 2 and ends on June 21, which is about three days later than 'Cavendish' and four days later than 'Honeoye'. As shown in Table 2, the flower truss of 'Brunswick' is longer than for 'Cavendish' and 'Honeoye'. 'Brunswick' flowers typically open slightly beneath the leaf canopy. 'Brunswick' flower trusses produce more flowers than trusses of 'Cavendish' and 'Honeoye'. Flowers of 'Brunswick' and the reference varieties are white. The anther color is Yellow-Orange Group 17A. Secondary flowers of 'Brunswick' are similar to 'Honeoye' in size but larger than 'Cavendish'. Secondary flowers of 'Brunswick' typically have 5 or 6 petals while 'Cavendish' usually has 6 petals and 'Honeoye' has 5. The petals of 'Brunswick' are slightly longer than wide whereas petals of 'Cavendish' and 'Honeoye' are as long as wide. The inner calyx of 'Brunswick' has a smaller diameter than the outer calyx while for 'Cavendish' and 'Honeoye' the inner and outer calyces have a similar diameter. Trusses of 'Brunswick' and 'Honeoye' are typically semi-erect at first picking in contrast to 'Cavendish' which is prostrate. The position of the calyx is even with the top of the berry for 'Brunswick'. The adherence of the calyx to the fruit is weak to medium for 'Brunswick' and 'Honeoye' but strong for 'Cavendish'. The fruit of 'Brunswick' are slightly larger than for 'Honeoye' but smaller than 'Cavendish'. The ratio of fruit length to width is 0.82 for 'Brunswick', 0.92 for 'Cavendish' and 0.97 for 'Honeoye'. 'Brunswick' fruit are ovoid to short-conic in shape. Fruit of all three varieties are medium in firmness. For 'Brunswick', the hollow center size ranges from zero in small tertiary fruit, to 1–3 mm (diameter) in medium-sized tertiary fruit, to 3–6 mm in large primary fruit. As shown in Table 2, the exterior fruit color of 'Brunswick' is Red Group 46A and on the inside the pith and cortex are Red Group 45B, indicating very even interior color. The reference varieties have a very similar color to 'Brunswick'. The achenes of 'Brunswick' are Green-Yellow Group 1A but darken to Orange-Red Group 34A on the shoulders of the fruit when exposed to sunlight.

TABLE 2

Flower and Fruit Characteristics for 'Brunswick', 'Cavendish' and 'Honeoye'

| Character | Cultivar 'Brunswick' | 'Cavendish' | 'Honeoye' |
|---|---|---|---|
| Flower position (relative to leaf canopy) | slightly beneath | beneath | slightly beneath |
| Flower truss length | medium | short–medium | short–medium |
| (cm) | 24.2 | 20.4 | 21.8 |
| Number of flowers/truss | 8.1 | 6.4 | 6.7 |
| Number of petals | 5.4 | 6.0 | 5.1 |
| Flower size (mm diameter) | 31.1 | 27.0 | 30.1 |
| Flower color | White | White | White |
| Petal length (mm) | 12.2 | 10.6 | 12.0 |
| Petal width (mm) | 11.6 | 10.5 | 12.0 |
| Petal spacing | spaced to touching | touching to overlapping | spaced to touching |
| Calyx size | | | |
| Inner calyx (mm diam.) | 24.4 | 22.8 | 23.1 |
| Outer calyx (mm diam.) | 26.7 | 22.4 | 23.8 |
| Calyx position | even | even to in a basin | even to slightly above |
| Adherence of the calyx | weak to medium | strong | weak to medium |
| Fruit size and shape | | | |
| Length (mm) | 28.1 | 31.8 | 29.9 |
| Width (mm) | 34.4 | 34.6 | 30.7 |
| Length/width ratio | 0.82 | 0.92 | 0.97 |
| Subjective fruit shape | ovoid to short-conic | cordate | short-conic |
| Seed position | slight-indent | slight-indent | slight indent |
| Fruit firmness | medium | medium | medium |
| Color (R.H.S. Colour Chart) | | | |
| Calyx | Green Group 137C to 137D | Green Group 137C | Green Group 137C |
| Fruit exterior | Red Group 46A | Red Group 46A | Red Group 46A |
| Fruit interior | Red Group | Red Group | Red Group |
| Pith | 45B | 45B | 45B |
| Cortex | 45B | 45B | 45B |

Disease resistance: 'Brunswick' and 'Cavendish' are resistant to red stele root rot (*Phytophthora fragariae*) while 'Honeoye' is susceptible. 'Brunswick' plants are slightly more resistant to powdery mildew (*Sphaerotheca macularis*) than 'Cavendish' and 'Honeoye', which are susceptible. 'Brunswick' and 'Cavendish' are susceptible to green petal phytoplasma while 'Honeoye' is resistant.

Production characteristics: 'Brunswick' has produced high yields; generally similar to 'Cavendish' and 'Honeoye', as shown in Table 3. The proportion of fruit considered marketable is similar between the three varieties. The fruit of 'Brunswick' are larger (by weight) than 'Honeoye' but smaller than 'Cavendish'. The mean harvest date for 'Brunswick' is similar to 'Cavendish' and 'Honeoye'. All three varieties have a harvest season which is early-midseason.

TABLE 3

Performance of 'Brunswick' and 'Cavendish' or 'Honeoye' in 1997 and 1998 Averaged over Several Sites*

| | Total Yield (t/ha) | % Yield marketable | Size (g/fruit) | Mean Harvest (day of year) |
|---|---|---|---|---|
| 1997 (five sites) | | | | |
| 'Brunswick' | 7.2 | 87.9 | 13.3 | 201.7 |
| 'Cavendish' | 5.4 | 90.8 | 14.7 | 201.5 |
| 1998 (four sites) | | | | |
| 'Brunswick' | 9.9 | 81.1 | 11.2 | 188.2 |
| 'Cavendish' | 8.6 | 81.2 | 11.6 | 189.2 |
| 1998 (one site) | | | | |
| 'Brunswick' | 17.1 | 94.2 | 12.8 | 181.0 |
| 'Honeoye' | 15.8 | 96.1 | 10.8 | 182.8 |

*Kentville NS, Charlottetown PEI, Fredericton NB, Buctouche NB, and Pynn's Brook Nfld. Plants were grown in matted rows and three blocks of 3 m long rows were harvested at each site.

I claim:

1. The new and distinct variety of strawberry plant named 'Brunswick' as described and illustrated.

* * * * *

UNITED STATES PATENT AND TRADEMARK OFFICE

CERTIFICATE OF CORRECTION

PATENT NO. : PP 16,859 P3
APPLICATION NO. : 10/770360
DATED : July 25, 2006
INVENTOR(S) : Jamieson It is certified that error appears in the above-identified patent and that said Letters Patent is hereby corrected as shown below:

Title page, Item (73) Assignee, fourth line, "HortIculutre" should read -- Horticulture --

Signed and Sealed this

Twelfth Day of December, 2006

JON W. DUDAS
*Director of the United States Patent and Trademark Office*